United States Patent
Zanella et al.

(10) Patent No.: US 11,141,371 B2
(45) Date of Patent: Oct. 12, 2021

(54) **EXTRACTS OF *NANNOCHLOROPSIS* SP. AND THEIR APPLICATIONS**

(71) Applicant: Cutech SRL, Padua (IT)

(72) Inventors: Lorenzo Zanella, Mestre-Venezia (IT); Paolo Pertile, San Pietro Viminario (IT)

(73) Assignee: Symrise AG, Holzminden (DE)

( * ) Notice: Subject to any disclaimer, the term of this patent is extended or adjusted under 35 U.S.C. 154(b) by 881 days.

(21) Appl. No.: 15/504,055

(22) PCT Filed: Aug. 8, 2015

(86) PCT No.: PCT/EP2015/068320
§ 371 (c)(1),
(2) Date: Feb. 15, 2017

(87) PCT Pub. No.: WO2016/026723
PCT Pub. Date: Feb. 25, 2016

(65) Prior Publication Data
US 2017/0246229 A1    Aug. 31, 2017

(30) Foreign Application Priority Data

Aug. 19, 2014  (EP) ..................................... 14181355

(51) Int. Cl.
| | | |
|---|---|---|
| *A61K 8/9706* | (2017.01) | |
| *A61Q 7/00* | (2006.01) | |
| *A61Q 19/00* | (2006.01) | |
| *A61K 8/9767* | (2017.01) | |
| *A61K 8/9771* | (2017.01) | |
| *A61K 8/9789* | (2017.01) | |
| *A61K 8/9794* | (2017.01) | |
| *A61K 36/05* | (2006.01) | |
| *A61Q 5/00* | (2006.01) | |
| *A61Q 5/10* | (2006.01) | |

(52) U.S. Cl.
CPC .......... *A61K 8/9706* (2017.08); *A61K 8/9767* (2017.08); *A61K 8/9771* (2017.08); *A61K 8/9789* (2017.08); *A61K 8/9794* (2017.08); *A61K 36/05* (2013.01); *A61Q 5/006* (2013.01); *A61Q 7/00* (2013.01); *A61Q 19/00* (2013.01); *A61Q 19/008* (2013.01); *A61K 2236/33* (2013.01); *A61K 2236/331* (2013.01); *A61K 2236/37* (2013.01); *A61Q 5/10* (2013.01)

(58) Field of Classification Search
CPC ................ A61K 36/00; A61K 2236/33; A61K 2236/331; A61K 2236/37; A61K 36/05; A61K 8/9706; A61K 8/975; A61K 8/9767; A61K 8/9771; A61K 8/9789; A61K 8/9794; A61Q 19/00; A61Q 19/008; A61Q 5/006; A61Q 5/10; A61Q 7/00; A61P 17/00; A61P 17/08; A61P 17/10; A61P 17/14
USPC ...................................................... 424/195.18
See application file for complete search history.

(56) References Cited

U.S. PATENT DOCUMENTS

| | | | | |
|---|---|---|---|---|
| 5,620,962 | A * | 4/1997 | Winget | .................. A61K 31/70 514/25 |
| 2008/0292851 | A1 | 11/2008 | Zimmerman et al. | |
| 2013/0129775 | A1 | 5/2013 | Shinde et al. | |

FOREIGN PATENT DOCUMENTS

| | | | | |
|---|---|---|---|---|
| JP | 2006232766 A | * | 9/2006 | |
| WO | 03/105791 A1 | | 12/2003 | |
| WO | WO-03105791 A1 | * | 12/2003 | ............... A61K 8/31 |

OTHER PUBLICATIONS

"Algae-derived skin tightener," Research Disclosure, Mason Publications, Hampshire, GB, vol. 519, No. 7, Jul. 1, 2007, p. 656.

\* cited by examiner

*Primary Examiner* — Aaron J Kosar

(74) *Attorney, Agent, or Firm* — Dilworth & Barrese, LLP

(57) ABSTRACT

New extracts of *Nannochloropsis* sp. and related species of *Nannochloropsis* are suggested, obtainable by treating said microalgae with a solvent selected from the group consisting of $C_1$-$C_1$ aliphatic alcohols, ethyl acetate, water or their mixtures, removing the dissolved extracts from the residues and recovering the pure extracts from the solvent. The extracts show excellent properties particularly in modulating the metabolism of human skin and hair follicles.

7 Claims, No Drawings

EXTRACTS OF *NANNOCHLOROPSIS* SP. AND THEIR APPLICATIONS

FIELD OF INVENTION

The present invention relates to the area of cosmetics and toiletries and refers to extracts of microalgae belonging to the genus *Nannochloropsis*, processes and compositions for obtaining them, and their use in hair and skin care applications.

STATE OF THE ART

Throughout the last decades, the cosmetics and toiletries industry has demonstrated increasing interest in the identification of natural compounds suitable for use in the preparation of body care products, with special attention to anti-aging products. Natural organisms, in particular plants and their fruits, represent an important source of active compounds for a rapidly expanding market sector.

Plants are the main source of natural actives, on a quantitative basis, with particular reference to antioxidants, vitamins and micronutrients. Many of these active compounds have been shown to protect the body from aging processes and environmental damage. Different risk factors affecting human health, e.g. skin exposure to UV radiation or excessive production of free radicals due to a wrong lifestyle, can be similarly mitigated by abundant vegetables in the diet.

Treatment of the skin represents the main field of application for natural actives, also because the skin is an organ whose appearance depends on different characteristics: color, smoothness, thickness of the epidermal stratum corneum, presence of wrinkles or spots, presence of hairs, production of sebum etc. As a consequence, specific and differentiated products can be formulated in order to modulate the tissue processes that affect each of these skin features.

Among the relevant issues for cosmetic exploitation of natural extracts is modulation of the skin pigmentation. While the Western world considers anti-aging to be a major criterion for defining beauty, it is associated to skin color in several Asian countries. Melanocytes are the cells specifically responsible for melanin production in the skin and its annexes. Potential modulators of melanin biosynthesis have to be considered of great interest for both cosmetic and medical applications. Skin lightening cosmetics meet the requirements of an increasing number of consumers by responding to the aesthetic desire of many people in Japan and other Asian countries. However, skin lightening products are also applied in the treatment of skin disorders, such as melasma, a skin condition in which brown patches occur primarily on the cheekbones, forehead and upper lip. This problem is more frequent among people with a colored skin, including Asians. Among customers in the Western world, skin lightening products are also appreciated to prevent or inhibit face spots, including brown spots and freckles.

Another important cosmetic sector is related to hair care. Products for treating problems of the hair follicle, primarily hair loss and pigmentation issues, account for a total market of more than 10 billion US$ annually, despite a lack of truly effective solutions. Hair loss represents the main problem to be solved and, presently, the 5-alpha-reductase inhibitors are considered the more active agents. 5-alpha-reductase is the key enzyme involved in the transformation of testosterone to dihydrotestosterone (DHT), considered the main steroid compound responsible for hair loss in androgenetic alopecia. The active products, commercially available as Minoxidil (Rogaine), Finasteride (Propecia) and Dutasteride (Avodart), have to be administered under medical supervision and cannot be used to treat pregnant women. They can produce several undesired effects while satisfactory results are not guaranteed. Herbal preparations claiming to induce hair growth are available at a low cost, but their effectiveness is usually very limited.

Unwanted hair is another cosmetic issue, and the disclosure of new non-toxic agents inhibiting hair growth would find ready applications. The disclosure of active ingredients able to modulate the hair follicle metabolism can therefore be usefully exploited by the cosmetics industry whatever their activity, i.e. either that they stimulate or inhibit hair growth.

Nowadays, modulation of the lipid metabolism also assumes primary importance for improving the personal appearance. The modern lifestyle, characterized by sedentary work often associated with wrong nutritional behavior, has broadly promoted an excessive accumulation of body fat. Many people suffer from this problem with serious consequences not only on their looks and social relationships, but also on their health and life expectancy. There are few solutions in this regard apart from severe slimming diets, fatiguing exercises, or dangerous and invasive interventions of aesthetic surgery. On the other hand, people of normal weight can also be affected by fat deposition localized in the skin subcutis of particular body regions. Cellulite, for instance, can be considered a typical problem related with this unbalanced fat metabolism, scientifically defined as "lipodystrophy" or "edematousfibrosclerotic panniculopathy". Very few cosmetic treatments are presently available for reducing the subcutaneous fatty layer, also referred as subcutis. The cosmetics industry is very interested in the disclosure of effective compounds suitable to prevent the general accumulation of fat in the body, as well as to promote lipolysis in the subcutaneous tissue of the skin.

Interestingly, agents suitable to modulate the lipogenic processes can also find application in the treatment of skin affected by over-active sebaceous glands (oily skin). While the hypodermal fat is composed of adipocytes, i.e. cells specialized in the synthesis and storage of lipids, the sebaceous glands are composed of sebocytes, which synthesize lipids aimed to be released on the skin surface when they undergo a differentiation process. At the end of the differentiation, sebocytes die and spill their contents (sebum) into the gland lumen, from where this is secreted to the skin surface. Therefore, although lipid synthesis is the specific activity of both adipocytes and sebocytes, their biological function is fundamentally different and the related regulation mechanisms might be completely different. As a consequence, it would not be surprising that an inhibitor of the adipocyte metabolism (i.e. the accumulation of lipids) is also able to stimulate sebocyte activity, or vice-versa.

The overproduction of sebum by sebaceous glands of the scalp is the cause of greasy hair, which is considered an aesthetic problem. Many cosmetic treatments, in the form of medicated shampoos and lotions, are proposed to calm the scalp's overproduction of sebum. However, cosmetics companies are continuously seeking new products, especially if obtained with natural ingredients. The seborrhea is involved in the occurrence of dandruff, a disorder of the scalp characterized by patches of abundant and loosely adherent flakes, usually accompanied by itching. This accentuated desquamation of the scalp can evolve into seborrheic dermatitis, which appears as a severe form of dandruff accompanied by inflammation and erythema. The etiology of dandruff and seborrheic dermatitis appears to be dependent upon three factors: sebaceous gland secretions, micro-flora metabolism, and individual susceptibility. The regulation of sebum production is therefore a pivotal issue for the prevention of dandruff and seborrheic dermatitis, and the present invention is related with this problem, among others.

Undesirable hyperactivity of the sebaceous glands can also occur in other parts of the body, especially on the face. Here the overproduction of sebum gives the skin a shiny and aesthetically undesirable appearance (oily skin) and can promote other slight blemishes, such as comedones. In some cases, more serious disorders can occur in the presence of excessive sebum, such as acne, a skin disease characterized by an inflammatory process of the hair follicle and annexed sebaceous gland. *Propionibacterium acnes* is considered to be the infectious agent in acne.

*P. acnes* is an aerotolerant anaerobic bacterium that lives deep within follicles and pores, using sebum, cellular debris and metabolic byproducts from the surrounding skin tissue as its primary sources of energy and nutrients. Elevated production of sebum by hyperactive sebaceous glands or blockage of the follicle can favor *P. acnes* bacteria proliferation, causing the inflamed pustules (pimples) characteristic of acne. As a consequence, the cosmetics industry is greatly interested in acquiring compounds that can inhibit sebum production, especially if this activity is combined with anti-inflammatory properties. However, anti-inflammatory action represents an appreciated additional value for each cosmetic application, since sensitization to many cosmetic ingredients and skin irritation are a relevant dermo-cosmetic issue.

Finally, compounds able to regulate sebum production can also find application in products for intimate hygiene, since the female external genitals have many sebaceous glands. Mons pubis, labia majora, labia minora and the external side of the vaginal vestibule are rich in sebaceous glands and their sebum secretion interacts with the bacterial microflora, regulating the pH of the genital area. The fresh sebum does not contain significant quantities of free fatty acids, but these are released as an effect of the lipases produced by bacteria, inducing the acidification of the genital environment. The regulation of sebum can therefore represent an important condition for preventing alterations of the genital microflora, irritations, itching, etc.

The present invention is the result of a major research effort aimed to discover natural substances or extracts suitable to offer natural and safe solutions to some of the skin problems mentioned herein.

This invention refers to the exploitation of the microalgae *Nannochloropsis* sp., belonging to the Eustigmataceae family (phylum: Heterokonta), as source of extracts exploitable for developing products aimed to:
  improve the health of hair and prevent hair loss;
  modulate the skin melanogenesis;
  modulate synthesis and secretion of sebum;
  modulate adipogenesis;
  exert anti-inflammatory activity.

The prior art related to the microalgae exploitation in the field of cosmetics offers several examples, but very few with regard to the species considered here.

The anti-free-radical activity of liquid extracts obtainable from Chlorophyceae, Prasinophyceae, Cryptophyceae, Bacillariophyceae (or diatoms) and Prymnesiophyceae was disclosed in FR 2657012 B1 (Secma) in 1990. The exploitability of Chaetoceros for cosmetic products has been known since 1975 thanks to GB 1392131 A (Aubert et al.). The Japanese patent JP 3822959 B2 (Noevir KK) refers to skin lotions effective for preventing skin wrinkles comprising an extract of certain diatoms, particularly Chaetoceros. The extraction solvent is selected from ethanol, methanol, 1,3-butylene glycol, water and is used in a single form or a two or more mixed form. In a preferred formulation, these solvents include an inorganic salt and a surfactant. U.S. Pat. No. 5,767,095 (Winget Rodner) discloses topical anti-inflammatory compositions comprising monogalactosyl-dieicosapentanoyl glycerol obtained from Chaetoceros and *Thalassiosira*, among others. According to EP 1808483 A1 (Cognis) Chlorococcum citriforme has been considered an interesting source of lutein for cosmetic applications. International patent application WO 1997/034489 A1 (Aquaculture Technology) refers to the use of extracts obtained from the marine algae Chaetoceros or *Thalassiosira* as antibacterially active agents and to compositions containing such agents for use against pathogenic bacteria. International patent application WO 2010/0029115 A1 (LVHM Recherche) proposes the use of certain natural extracts, for example obtained from *Thalassiosira*, for reducing skin and hair pigmentation. Several cosmetic applications (including modulation of skin pigmentation, stratum corneum differentiation, hair growth and fat metabolism) are disclosed by Cutech (WO 2012/052356 A2) for extracts obtained from Monodus, *Thalassiosira*, Chaetoceros and Chlorococcum.

FR 2894473 A1 (Daniel Jouvance) discloses the use of preparations obtained from some microalgae (Chromulina, Asterionella and *Tetraselmis*) for inhibiting the enzymes involved in the metabolism of fatty acids and lipids. Slimming preparations from several species of macro-algae are proposed in the Japanese patent JP 2000072642 A (Lion), however, no prior art is available with regard to fat metabolism modulation based on agents from the microalgae considered here.

The only significant prior art on *Nannochloropsis* is represented by JP 2006232766 A (Pentapharm), which refers to aqueous extracts obtained from these microalgae providing excellent anti-oxidizing stress actions on skin, tightening effects and alleviating aging signs such as flabbiness or wrinkles. However, the Pentapharm invention is limited to the typical skin antiaging application. The prior art is completely silent on cosmetic applications aimed to modulate skin pigmentation, hair metabolism, fat tissue and sebaceous glands metabolism.

Therefore, the object of the present invention has been to develop extracts based on renewable sources, more particularly on microalgae belonging to the genus *Nannochloropsis*, suitable to modulate the metabolism of human skin melanocytes, hair follicles, hypodermal adipocytes and human sebaceous glands. In particular, it has been the object of the present invention to develop new extracts for cosmetic and the respective dermatological applications, which simultaneously modulate, i.e. increase, reduce, improve and/or stimulate:
  melanogenesis in human hair and skin;
  growth or alternatively inhibition of growth of human hair and hair follicles;
  lipolysis;
  sebocyte metabolism;
  inflammatory processes of the skin.

DESCRIPTION OF THE INVENTION

A first preparation of the present invention refers to extracts of *Nannochloropsis* sp. obtainable by treating dried cell material with a solvent selected from the group consisting of $C_1$-$C_4$ aliphatic alcohols, ethyl acetate, water or their mixtures, removing the dissolved extracts from the residues and recovering the pure extracts from the solvent.

Surprisingly, it has been found that the said extracts fulfil the complex profile explained above. In particular, they are suitable for increasing, reducing, improving and/or stimulating melanogenesis in human hair and skin; growth or alternatively inhibition of growth of human hair and hair follicles; lipolysis; sebocyte metabolism; and inflammatory processes of the skin.

Microalgae

According to the present invention, the *Nannocholoropsis* microalgae have been identified as being suitable to solve the complex profile explained above.

*Nannochloropsis* sp.

*Nannochloropsis*, belonging to the class Eustigmatophyceae, is a microalga genus rich in polyunsaturated fatty acids, mainly occurring in the marine environment but also in fresh and brackish water. They are small, nonmotile spheres that do not show any distinctive morphological trait, so that their systematic characterisation is generally done by genetic analysis.

The biological material adopted for the present invention was a freeze-dried biomass of an undetermined *Nannochloropsis* (*Nannochloropsis* sp.), however, the preferred strain for the proposed application is *Nannochloropsis oceanica*.

The suitable strains of *Nannochloropsis* with respect to the present invention are: *Nannochloropsis gaditana, N. granulata, N. limnetica, N. oceanica N. oculata, N. salina.*

Extraction Process of Microalgae

Another object of the present invention relates to a process for obtaining extracts of *Nannochloropsis* sp. comprising the following steps:
(a) bringing said microalgae in contact with a solvent selected from the group consisting of $C_1$-$C_4$ aliphatic alcohols, ethyl acetate, water or their mixtures in an amount suitable to cause the actives to move into the solvent phase, optionally at elevated temperatures,
(b) removing the dissolved extract from the residue, and
(c) recovering the pure extract from the solvent.

The microalgal biomass can be obtained by cultivation in photobioreactors, large polyethylene bags, tanks or open ponds, in daylight or artificial light. The cultivation can occur indoors or outdoors. Some microalgal strains can be also cultivated in heterotrophic conditions, in the dark, in appropriate bioreactors.

When the microalgal biomass reaches a suitable cell density, it can be harvested by centrifugation, sedimentation, flocculation, or with other techniques that can preserve the integrity of the cell material. The harvested biomass is freeze dried and packaged in vacuum sealed plastic bags or aluminum foil bags, then frozen and preserved at −20° C. till the time of extraction.

Basically, the extracts according to the present invention may be prepared by known methods, for example, by aqueous, organic or aqueous/organic extraction of the microalgae using the solvents explained hereinafter. Suitable extraction processes are any conventional process such as maceration, re-maceration, digestion, agitation maceration, vortex extraction, ultrasonic extraction, counter current extraction, percolation, re-percolation, evacolation (extraction under reduced pressure), diacolation and solid/liquid extraction under continuous reflux. Percolation is advantageous for industrial uses. Any size reduction methods known to the expert, for example, freeze grinding, may be used. Preferred solvents for the extraction process are methanol, ethanol, isopropyl alcohol, ethyl acetate, hexane and water (preferably hot water at a temperature above 80° C., and even more so above 95° C.) or mixtures of said organic solvents and water, more particularly, low molecular weight alcohols with more or less high water contents. An extraction with methanol, ethanol and water-containing mixtures thereof is particularly preferred. The extraction process is generally conducted at temperatures from about 10 to about 100° C. In one preferred preparation, the extraction process is conducted in an inert gas atmosphere to avoid oxidation of the extract ingredients. This is particularly important where extraction is done at temperatures above 40° C. The extraction times are selected depending on the starting material, extraction process, extraction temperature, and ratio of solvent to raw material, etc. After the extraction process, the crude extracts obtained may optionally be subjected to other typical steps, such as purification, concentration and/or decoloration. If desired, the extracts thus prepared may be subjected, for example, to the selective removal of individually unwanted ingredients. The extraction process may be conducted to any degree, but is usually continued to exhaustion. Typical yields (=extract dry matter based on the quantity of raw material used) in the extraction of the starting materials are in the order of from about 1 to about 50%, preferably from about 5 to about 30%, and even more preferably from about 10 to about 20% b.w.—calculated on the starting materials.

The typical process for obtaining the microalgae extracts according to the invention is described in more detail in the following:
- each gram of dry biomass was extracted by treatment with 100 ml of solvent, stirring the suspension at room temperature for 16 hours in the dark;
- the residual cell material was separated from the extract by centrifugation at 2000 G for 15 minutes;
- the residual biomass was washed by suspending it in 50 ml of solvent;
- the cell material was separated from the washing solvent by centrifugation at 2000 G for 15 minutes;
- the residual biomass was washed again by suspending it in 50 ml of solvent;
- the cell material was separated from the washing solvent by centrifugation at 2000 G for 15 minutes;
- the firstly collected extract and the washing solvent volumes were mixed, and the resulting extract was considered to have a conventional concentration of 5000 µg/ml (1000 mg of dry algae in 200 ml of solvent).

According to the present invention, cell material of the aforementioned microalgae was extracted with a liquid extractant selected from the group consisting of ethyl acetate, isopropanol, ethanol, methanol and water.

The extractant can also comprise a mixture of two or more of the above solvents. Hereinafter, the microalgae extract concentrations will be conventionally expressed as the ratio between the quantity (in weight) of cell material treated and the extractive solvent (in volume). For instance, by treating 1 g of dry powered microalgae with 200 ml of extractive solvent, 200 ml of extract at 5000 µg/ml (w/v) are obtained without regard for the quantity of compounds really solubilized in the solvent. This conventional concentration allows representation of the quantity of dried microalgae effectively required to produce the experimental results described. However, the estimated dry weights of the extracts are reported in Table 1 and the real extract concentration can be calculated. As the composition of the microalgae may change in relation to culture methods and environmental conditions, the extraction efficacy may also change, so the extract dry weights have to be considered as rough indications.

Quantity and quality of compounds present in the extracts may vary with respect to both solvent properties and preparation protocol. The dry weights of the prepared extracts expressed as percentage of the related integral microalgae material are reported in Table 1. For obtaining extracts of *Nannochloropsis* sp. the following steps are proposed:

(a) bringing said microalgae in contact with a solvent selected from the group consisting of $C_1$-$C_4$ aliphatic alcohols, ethyl acetate, water or their mixtures in an amount suitable to cause the actives to move into the solvent phase, optionally at elevated temperatures,
(b) removing the dissolved extract from the residue, and
(c) recovering the pure extract from the solvent.

TABLE 1

Dry weight of the extracts expressed as percentage of the dry cell material of *Nannochloropsis* sp.

| Extract code | *Nannochloropsis* sp. |
| --- | --- |
| Methanol | 40% |
| Ethanol | 30% |
| Isopropyl alcohol | 18% |
| Ethyl acetate | 10.5% |
| Water | 55% |

Extracts can be obtained adopting the protocol reported above also using a mixture of the cited solvents.

INDUSTRIAL APPLICATION

Another object of the present invention is directed at cosmetic and personal care compositions comprising extracts of microalgae or plants and a cosmetically acceptable carrier selected from the group consisting of $C_1$-$C_4$ aliphatic alcohols, polyols having 3 to 12 carbon atoms, oil components, water and their mixtures. Suitable carriers encompass, for example, ethanol, propanol, isopropyl alcohol, all isomeric forms of butanol, ethylene and/or propylene glycol and its dimers and trimers, glycerol, glucose, pentaerythritol and the like. Suitable oil components are disclosed in the following chapter.

The compositions may contain the extracts in amounts of from 0.001 to 35, preferably from 0.5 to 20, and more preferably from 1 to 10% b.w.—the amounts calculated on the dry matter of the extracts. The remaining parts are the carriers. Typically, the administration of the extracts takes place topically; however, it is also possible to use the extracts—especially after encapsulation—for oral uptake.

Cosmetic or Personal Care Composition

Another object of the present invention encompasses a cosmetic or personal care composition, comprising
(i) an extract according to the invention and
(ii) a cosmetically acceptable carrier selected from the group consisting of $C_1$-$C_4$ aliphatic alcohols, polyols having 3 to 12 carbon atoms, oil components, water and their mixtures.

The cosmetic or personal care composition may represent a skin care, hair care and/or sun care product, such as for example a cosmetic cream, lotion, spray, emulsion, ointment, gel or mouse and the like. Typical examples are skin creams and hair shampoos, antiperspirants and soaps.

The preparations according to the invention may contain abrasives, anti-acne agents, agents against ageing of the skin, anti-cellulitis agents, antidandruff agents, anti-inflammatory agents, irritation-preventing agents, irritation-inhibiting agents, antioxidants, astringents, perspiration-inhibiting agents, antiseptic agents, ant-statics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, hair promotion agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxy acids, polyhydroxyfatty acids, liquefiers, dyestuffs, colour-protecting agents, pigments, anti-corrosives, aromas, flavouring substances, odoriferous substances, polyols, surfactants, electrolytes, organic solvents or silicone derivatives and the like as additional auxiliaries and additives.

Surfactans

Preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineralöladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other surfactants may also be added to the preparations as emulsifiers, including for example:

products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial Glycerides.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan Esters.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol esters. Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Poly-glyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic Emulsifiers.

Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric Emulsifiers.

Other suitable emulsifiers are amphboteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bisdimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlizing Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consistiung of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivativesand indole derivatives.

In addition, it is advantageous to combine compounds of formula (I) with active ingredients which penetrate into the skin and protect the skin cells from inside against sunlight-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of p-aminobenzoic acid p-aminobenzoic acid ethyl ester (25 mol) ethoxylated (INCI name: PEG-25 PABA)

p-dimethylaminobenzoic acid-2-ethylhexyl ester p-aminobenzoic acid ethyl ester (2 mol) N-propoxylated p-aminobenzoic acid glycerol ester salicylic acid homomenthyl ester (homosalates) (Neo Heliopan® HMS)

salicylic acid-2-ethylhexyl ester (Neo Heliopan® OS)

triethanolamine salicylate 4-isopropyl benzyl salicylate anthranilic acid menthyl ester (Neo Heliopan® MA)

diisopropyl cinnamic acid ethyl ester p-methoxycinnamic acid-2-ethylhexyl ester (Neo Heliopan® AV)

diisopropyl cinnamic acid methyl ester p-methoxycinnamic acid isoamyl ester (Neo Heliopan® E 1000)

p-methoxycinnamic acid diethanolamine salt p-methoxycinnamic acid isopropyl ester 2-phenylbenzimidazole sulfonic acid and salts (Neo Heliopan® Hydro)

3-(4'-trimethylammonium) benzylidene bornan-2-one methyl sulfate beta-imidazole-4(5)-acrylic acid (urocanic acid)

3-(4'-sulfo)benzylidene bornan-2-one and salts 3-(4'-methyl benzylidene)-D,L-camphor (Neo Heliopan® MBC)

3-benzylidene-D,L-camphor

N-[(2 and 4)-[2-(oxoborn-3-ylidene)methyl]benzyl]acrylamide polymer 4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb® HEB)

benzylidene malonate polysiloxane (Parsol® SLX)

glyceryl ethylhexanoate dimethoxycinnamate dipropylene glycol salicylate tris(2-ethylhexyl)-4,4',4"-(1,3,5-triazine-2,4,6-triyltriimino) tribenzoate (=2,4,6-trianilino-(p-carbo-2'-ethylhexyl-1'-oxy)-1,3,5-triazine) (Uvinul® T150).

Broadband filters which are preferably combined with one or more compounds of formula (I) in a preparation according to the present invention are selected from the group consisting of 2-ethylhexyl-2-cyano-3,3-diphenyl acrylate (Neo Heliopan® 303)

ethyl-2-cyano-3,3'-diphenyl acrylate 2-hydroxy-4-methoxybenzophenone (Neo Heliopan® BB)

2-hydroxy-4-methoxybenzophenone-5-sulfonic acid dihydroxy-4-methoxybenzophenone 2,4-dihydroxybenzophenone tetrahydroxybenzophenone 2,2'-dihydroxy-4,4'-dimethoxybenzophenone 2-hydroxy-4-n-octoxybenzophenone 2-hydroxy-4-methoxy-4'-methyl benzophenone sodium hydroxymethoxybenzophenone sulfonate disodium-2,2'-dihydroxy-4,4'-dimethoxy-5,5'-disulfobenzophenone phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl®XL)

2,2'-methylene bis-(6-(2H-benzotriazol-2-yl)-4-1,1,3,3-tetramethylbutyl) phenol) (Tinosorb® M)
2,4-bis-[4-(2-ethylhexyloxy)-2-hydroxyphenyl]-1,3,5-triazine
2,4-bis-[{(4-(2-ethylhexyloxy)-2-hydroxy}phenyl]-6-(4-methoxyphenyl)-1,3,5-triazine (Tinosorb® S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxy}phenyl]-6-[4-(2-methoxyethyl carbonyl) phenylamino]-1,3,5-triazine
2,4-bis-[{4-(3-(2-propyloxy)-2-hydroxypropyloxy)-2-hydroxy}phenyl]-6-[4-(2-ethylcarboxyl) phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2"-methylpropenyloxy)-2-hydroxy}phenyl]-6-(4-methoxyphenyl)-1,3,5-triazine
2,4-bis-[{4-(1',1',1',3',5',5',5'-heptamethylsiloxy-2"-methyl-propyloxy)-2-hydroxy}phenyl]-6-(4-methoxyphenyl)-1,3,5-triazine.

The compositions can comprise further typical detergent and cleansing composition ingredients such as UV-A filters filters which are preferably combined with one or more compounds of formula (I) in a preparation according to the present invention are selected from the group consisting of
4-isopropyl dibenzoyl methane
terephthalylidene dibornane sulfonic acid and salts (Mexoryl® SX)
4-t-butyl-4'-methoxydibenzoyl methane (avobenzone)/(Neo Heliopan® 357)
phenylene bis-benzimidazyl tetrasulfonic acid disodium salt (Neo Heliopan® AP)
2,2'-(1,4-phenylene)-bis-(1H-benzimidazole-4,6-disulfonic acid), monosodium salt
2-(4-diethylamino-2-hydroxybenzoyl) benzoic acid hexyl ester (Uvinul® A Plus)
indanylidene compounds in accordance with DE 100 55 940 A1 (=WO 2002 038537 A1)

The compositions can comprise further typical detergent and cleansing composition ingredients such as UV filters which are more preferably combined with one or more compounds of formula (I) in a preparation according to the present invention are selected from the group consisting of
p-aminobenzoic acid
3-(4'-trimethylammonium) benzylidene bornan-2-one methyl sulfate
salicylic acid homomenthyl ester (Neo Heliopan® HMS)
2-hydroxy-4-methoxybenzophenone (Neo Heliopan® BB)
2-phenylbenzimidazole sulfonic acid (Neo Heliopan® Hydro)
terephthalylidene dibornane sulfonic acid and salts (Mexoryl® SX)
4-tert-butyl-4'-methoxydibenzoyl methane (Neo Heliopan® 357)
3-(4'-sulfo)benzylidene bornan-2-one and salts
2-ethylhexyl-2-cyano-3,3-diphenyl acrylate (Neo Heliopan® 303)
N-[(2 and 4)-[2-(oxoborn-3-ylidene) methyl]benzyl]acrylamide polymer
p-methoxycinnamic acid-2-ethylhexyl ester (Neo Heliopan® AV)
p-aminobenzoic acid ethyl ester (25 mol) ethoxylated (INCI name: PEG-25 PABA)
p-methoxycinnamic acid isoamyl ester (Neo Heliopan® E1000)
2,4,6-trianilino-(p-carbo-2'-ethylhexyl-1'-oxy)-1,3,5-triazine (Uvinul® T150)
phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl® XL)
4,4'-[(6-[4-(1,1-dimethyl)aminocarbonyl) phenylamino]-1, 3,5-triazine-2,4-diyl)diimino]-bis-(benzoic acid-2-ethylhexyl ester) (Uvasorb HEB)
3-(4'-methyl benzylidene)-D,L-camphor (Neo Heliopan® MBC)
3-benzylidene camphor
salicylic acid-2-ethylhexyl ester (Neo Heliopan® OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl) phenol) (Tinosorb® M)
phenylene bis-benzimidazyl tetrasulfonic acid disodium salt (Neo Heliopan® AP)
2,4-bis-[{(4-(2-ethylhexyloxy)-2-hydroxy}phenyl]-6-(4-methoxyphenyl)-1,3,5-triazine (Tinosorb® S)
benzylidene malonate polysiloxane (Parsol® SLX)
menthyl anthranilate (Neo Heliopan® MA)
2-(4-diethylamino-2-hydroxybenzoyl) benzoic acid hexyl ester (Uvinul® A Plus)
indanylidene compounds in accordance with DE 100 55 940 (=WO 02/38537).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Secondary Sun Protection Factors

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

Actives Modulating Skin and/or Hair Pigmentation

Preferred active ingredients for skin and/or hair lightening are selected from the group consisting of: kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), cyclohexylcarbamates (preferably one or more cyclohexyl carbamates disclosed in WO 2010/122178 and WO 2010/097480), sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, *papaya* extract, turmeric extract, mulberry extract, bengkoang extract, nutgrass extract, liquorice root extract or constituents concentrated or isolated therefrom, preferably glabridin or licochalcone A, *artocarpus* extract, extract of *rumex* and ramulus species, extracts of pine species (*pinus*), extracts of *vitis* species or stilbene derivatives isolated or concentrated therefrom, saxifrage extract, scutelleria extract, grape extract and/or microalgae extract, in particular *Tetraselmis suecica* Extract.

Preferred skin lighteners as component (b) are kojic acid and phenylethyl resorcinol as tyrosinase inhibitors, beta- and alpha-arbutin, hydroquinone, nicotinamide, dioic acid, Mg ascorbyl phosphate and vitamin C and its derivatives, mulberry extract, Bengkoang extract, *papaya* extract, turmeric extract, nutgrass extract, licorice extract (containing glycyrrhizin), alpha-hydroxy-acids, 4-alkylresorcinols, 4-hydroxyanisole. These skin lighteners are preferred due to their very good activity, in particular in combination with sclareolide according to the present invention. In addition, said preferred skin lighteners are readily available.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophyl-line and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate (Zn(Gly)2), manganese (II) bicarbonate complexes ("pseudocat-alases") as described for example in EP 0 584 178, tetrasubstituted cyclohexene deriva-tives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and ana-logues thereof, activators of adenylate cyclase and compounds which activate the transfer of melanosomes to keratinocytes such as serine proteases or agonists of the PAR-2 receptor, extracts of plants and plant parts of the chrysanthemum species, san-guisorba species, walnut extracts, urucum extracts, rhubarb extracts, microalgae extracts, in particular *Isochrysis galbana*, trehalose, erythru-lose and dihydroxyacetone. Flavonoids which bring about skin and hair tinting or brown-ing (e.g. quercetin, rhamnetin, kaempferol, fisetin, genistein, daidzein, chrysin and api-genin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

Anti-Ageing Actives

In the context of the invention, anti-ageing or biogenic agents are, for example antioxidants, matrix-metalloproteinase inhibitors (MMPI), skin moisturizing agents, glycosaminglycan stimulkators, anti-inflammatory agents, TRPV1 antagonists and plant extracts.

Antioxidants.

Suitable antioxidants encompass amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gammalinoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to μmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, ginkgo, ginseng, liquorice, honeysuckle, *sophora, pueraria, pinus*, citrus, Phyllanthus emblica or St. John's wort, grape seeds, wheat germ, Phyllanthus emblica, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

If vitamin E and/or derivatives thereof are used as the antioxidant(s), it is advantageous to choose their concentrations from the range from about 0.001 to about 10% b.w. based on the total weight of the formulation. If vitamin A or vitamin A derivatives or carotenes or derivatives thereof are used as the antioxidant(s), it is advantageous to choose their concentrations from the range from about 0.001 to about 10% b.w. based on the total weight of the formulation.

Matrix-Metalloproteinase Inhibitors (MMPI).

Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1(2H)benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-aminon-caproic acid of the serinprotease inhibitors: phenylmethylsufonylfluoride, collhibin (company Pentapharm; INCI: hydrolysed rice protein), oenotherol (company Soliance; INCI: propylene glycol, aqua, *Oenothera biennis* root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and lentinus *edodes* extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, particularly extracts of blackberry leaf (preferably as described in WO 2005 123101 A1, incorporated herein as reference) as e.g. SymMatrix (company Symrise, INCI: Maltodextrin, *Rubus Fruticosus* (Blackberry) Leaf Extract). Preferred actives are selected from the group consisting of retinyl palmitate, ursolic acid, extracts from the leaves of the Rosaceae family, sub-family Rosoideae, genistein and daidzein.

Skin-Moisturizing Agents.

Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.

Glycosaminoglycan Stimulators.

Preferred compositions comprise substances stimulating the synthesis of glycosaminoglycans selected from the group consisting of hyaluronic acid and derivatives or salts, Subliskin (Sederma, INCI: *Sinorhizobium Meliloti* Ferment Filtrate, Cetyl Hydroxyethylcellulose, Lecithin), Hyalufix (BASF, INCI: Water, Butylene Glycol, Alpinia galanga leaf extract, Xanthan Gum, Caprylic/Capric Triglyceride), Stimulhyal (Soliance, INCI: Calcium ketogluconate), Syn-Glycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, *Arctium lappa* fruit extract, *Eriobotrya japonica* extract, Genkwanin, N-Methyl-L-serine, (−)-alpha-bisabolol or synthetic alpha-bisabolol such as e.g. Dragosantol and Dragosantol 100 from Symrise, oat glucan, *Echinacea purpurea* extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, *Echinacea purpurea* extract, *Sinorhizobium Meliloti* Ferment Filtrate, Calcium ketogluconate, Alpinia galanga leaf extract and tetradecyl aminobutyroylvalylaminobutyric urea trifluoroacetate.

Anti-Inflammatory Agents.

The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, Aloe vera, *Commiphora* species, *Rubia* species, willow, willow-herb, oats, calendula, *arnica*, St John's wort, honeysuckle, rosemary, *Passiflora incarnata*, witch hazel, ginger or *Echinacea*; preferably selected from the group consisting of extracts or fractions from camomile, Aloe vera, oats, calendula, *arnica*, honeysuckle, rosemary, witch hazel, ginger or *Echinacea*, and/or pure substances, preferably alpha-bisabolol, apigenin, apigenin-7-glucoside, gingerols, shogaols, gingerdiols, dehydrogingerdiones, paradols, natural or naturally occuring avenanthramides, preferably tranilast, avenanthramide A, avenanthramide B, avenanthramide C, non-natural or non-naturally occuring avenanthramides, preferably dihydroavenanthramide D, dihydroavenanthramide E, avenanthramide D, avenan-thramide E, avenanthramide F, boswellic acid, phytosterols, glycyrrhizin, glabridin and licochalcone A; preferably selected from the group consisting of alphabisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and β-glucans, in particular 1,3-1,4-β-glucan from oats.

When bisabolol is used in the context of the present invention it can be of natural or synthetic origin, and is preferably "alpha-bisabolol". Preferably, the bisabolol used is synthetically prepared or natural (−)-alpha-bisabolol and/or synthetic mixed-isomer alphabisabolol. If natural (−)-alpha-bisabolol is used, this can also be employed as a constituent of an essential oil or of a plant extract or of a fraction thereof, for example as a constituent of (fractions of) oil or extracts of camomile or of Vanillosmopsis (in particular Vanillosmopsis erythropappa or Vanillosmopsis *arborea*). Synthetic alpha-bisabolol is obtainable, for example, under the name "Dragosantol" from Symrise.

In case ginger extract is used in the context of the present invention, preferably extracts of the fresh or dried ginger root are used which are prepared by extraction with methanol, ethanol, iso-propanol, acetone, ethyl acetate, carbon dioxide ($CO_2$), hexane, methylene chloride, chloroform or other solvents or solvent mixtures of comparable polarity. The extracts are characterized by the presence of active skin irritation-reducing amounts of constituents such as e.g. gingerols, shogaols, gingerdiols, dehydrogingerdiones and/or paradols.

TRPV1 Antagonists.

Suitable compounds which reduce the hypersensitivity of skin nerves based on their action as TRPV1 antagonists, encompass e.g. trans-4-tert-butyl cyclohexanol as described in WO 2009 087242 A1, or indirect modulators of TRPV1 by an activation of the μ-receptor, e.g. acetyl tetrapeptide-15, are preferred.

Desquamating Agents.

The compositions may also contain desquamating agents (component b5) in amounts of about 0.1 to about 30% b.w. preferably about 0.5 to about 15% b.w., particularly preferably about 1 to about 10% b.w. based on the total weight of the preparation. The expression "desquamating agent" is understood to mean any compound capable of acting:

either directly on desquamation by promoting exfoliation, such as β-hydroxy acids, in particular salicylic acid and its derivatives (including 5-n-octanoylsalicylic acid); α-hydroxy acids, such as glycolic, citric, lactic, tartaric, malic or mandelic acids; urea; gentisic acid; oligofucoses; cinnamic acid; extract of *Sophora japonica*; resveratrol and some derivatives of jasmonic acid;

or on the enzymes involved in the desquamation or the degradation of the corneodesmosomes, glycosidases, stratum corneum chymotryptic enzyme (SCCE) or other proteases (trypsin, chymotrypsin-like). There may be mentioned agents chelating inorganic salts: EDTA; N-acyl-N,N',N'-ethylenediaminetriacetic acid; aminosulphonic compounds and in particular (N-2-hydroxyethylpiperazine-N-2-ethane)sulphonic acid (HEPES); derivatives of 2-oxothiazolidine-4-carboxylic acid (procysteine); derivatives of alpha-amino acids of the glycine type (as described in EP-0 852 949, and sodium methylglycine diacetate marketed by BASF under the trade name TRILON M); honey; sugar derivatives such as 0-octanoyl-6-D-maltose and N-acetylglucosamine; chestnut extracts such as those marketed by the company SILAB under the name Recoverine®, prickly pear extracts such as those marketed under the name Exfolactive® by the company SILAB, or Phytosphingosine SLC® (phytosphingosine grafted with a salicylic acid) marketed by the company Degussa.

Desquamating agents suitable for the invention may be chosen in particular from the group comprising sulphonic acids, calcium chelators, α-hydroxy acids such as glycolic, citric, lactic, tartaric, malic or mandelic acids; ascorbic acid and its derivatives such as ascorbyl glucoside and magnesium ascorbyl phosphate; nicotinamide; urea; (N-2-hydroxyethylpiperazine-N-2-ethane)sulphonic acid (HEPES), β-hydroxy acids such as salicylic acid and its derivatives, retinoids such as retinol and its esters, retinal, retinoic acid and its derivatives, those described in the documents FR 2570377 A1, EP 0199636 A1, EP 0325540 A1, EP 0402072 A1, chestnut or prickly pear extracts, in particular marketed by SILAB; reducing compounds such as cysteine or cysteine precursors.

Desquamating agents which can be used are also nicotinic acid and its esters and nicotinamide, also called vitamin B3 or vitamin PP, and ascorbic acid and its precursors, as described in particular in application EP 1529522 A1.

Anti-Cellulite Agents.

Anti-cellulite agents and lipolytic agents are preferably selected from the group consisting of those described in WO 2007/077541, and beta-adrenergic receptor agonists such as synephrine and its derivatives, and cyclohexyl carbamates described in WO 2010/097479. Agents enhancing or boosting the activity of anti-cellulite agents, in particular agents which stimulate and/or depolarise C nerve fibres, are preferably selected from the group consisting of capsaicin and derivatives thereof, vanillyl-nonylamid and derivatives thereof, L-carnitine, coenzym A, isoflavonoides, soy extracts, *ananas* extract and conjugated linoleic acid.

Fat Enhancing Agents.

Formulations and products according to the present invention may also comprise one or more fat enhancing and/or adipogenic agents as well as agents enhancing or boosting the activity of fat enhancing agents. A fat enhancing agent is for example hydroxymethoxyphenyl propylmethylmethoxybenzofuran (trade name: Sym3D®).

Hair Growth Activators or Inhibitors

Formulations and products according to the present invention may also comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-beta-citronellol, panthenol, glycogen for example from mussels, extracts from microorganisms, algae, plants and plant parts of for example the genera dandelion (Leontodon or *Taraxacum*), Orthosiphon, Vitex, *Coffea, Paullinia, Theobroma, Asiasarum, Cucurbita* or Styphnolobium, Serenoa *repens* (saw palmetto), *Sophora flavescens, Pygeum africanum, Panicum miliaceum, Cimicifuga racemosa, Glycine max,* Eugenia caryophyllata, Cotinus coggygria, *Hibiscus rosasinensis, Camellia sinensis*, Ilex paraguariensis, *Isochrysis galbana*, licorice, grape, apple, barley or hops or/nd hydrolysates from rice or wheat.

Alternatively, formulations and products according to the present invention may comprise one or more hair growth inhibitors (as described above), i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gammaglutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera *Chondrus, Gloiopeltis, Ceramium, Durvillea, Glycine max, Sanguisorba officinalis, Calendula officinalis, Hamamelis virginiana, Arnica montana, Salix alba, Hypericum perforatum* or *Gymnema sylvestre*.

Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (I-menthoxy)-1,2-propandiol, (1-menthoxy)-2-methyl-1,2-propandiol, 1-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy) acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, monomenthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or N$^α$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide

[WS23]), isopulegol or its esters (I-(−)-isopulegol, I-(−)-isopulegolacetate), menthane derivatives (for example pmenthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxa mates (preferably those described in EP 2033688 A2).

Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or *styrax* or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, *galbanum* oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose. In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are

- glycerol;
- alkylene glycols such as, for example, ethylene glycol, diethylene glycol, propylene glycol, butylene glycol, hexylene glycol and polyethylene glycols with an average molecular weight of 100 to 1000 Dalton;
- technical oligoglycerol mixtures with a degree of self-condensation of 1.5 to 10, such as for example technical diglycerol mixtures with a diglycerol content of 40 to 50% by weight;
- methylol compounds such as, in particular, trimethylol ethane, trimethylol propane, trimethylol butane, pentaerythritol and dipentaerythritol;
- lower alkyl glucosides, particularly those containing 1 to 8 carbon atoms in the alkyl group, for example methyl and butyl glucoside;
- sugar alcohols containing 5 to 12 carbon atoms, for example sorbitol or mannitol,
- sugars containing 5 to 12 carbon atoms, for example glucose or sucrose;
- amino sugars, for example glucamine;
- dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (*galbanum*, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, .-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, *galbanum* oil, *ladanum* oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3$ $Fe_3O_4$, FeO (OH)) and/or tin oxide. Advantageous dyes are for example carmine, Berlin blue, chromium oxide green, ultramarine blue and/or manganese violet.

Preparations

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

Capsules and Micro-Capsules

For oral uptake, encapsulation of the extracts represents a preferred embodiment. Usually encapsulation can take place by using gelatine as a matrix. It is also possible to prepare capsules by adding a gelling agent such as, for example, alginate to the extracts and drop the mixture into a bath of a calcium salt. Both methods lead to macro-capsules having a diameter of from about 1 cm to about 5 cm which are toxicologically safe and suitable for consumption.

It may also be desired to encapsulate the extracts for the formulation of compositions which are developed for topical application. This can have different reasons: stabilisation against an interaction with other compounds in the formulation, protection against chemical degradation or simply for the preparation of a very aesthetical product. For this purpose, usually microcapsules are applied. "Microcapsules" are understood to be spherical aggregates with a diameter of from about 0.1 to about 5 mm which contain at least one solid or liquid core surrounded by at least one continuous membrane. More precisely, they are finely dispersed liquid or solid phases coated with film-forming polymers, in the production of which the polymers are deposited onto the material to be encapsulated after emulsification and coacervation or interfacial polymerization. In another process, liquid active principles are absorbed in a matrix ("microsponge") and, as microparticles, may be additionally coated with film-forming polymers. The microscopically small capsules, also known as nanocapsules, can be dried in the same way as powders. Besides single-core microcapsules, there are also multiple-core aggregates, also known as microspheres, which contain two or more cores distributed in the continuous membrane material. In addition, single-core or multiple-core microcapsules may be surrounded by an additional second, third, etc., membrane. The membrane may consist of natural, semisynthetic or synthetic materials. Natural membrane materials are, for example, gum arabic, agar agar, agarose, maltodextrins, alginic acid and salts thereof, for example sodium or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic membrane materials are inter alia chemically modified celluloses, more particularly cellulose esters and ethers, for example cellulose acetate, ethyl cellulose, hydroxypropyl cellulose, hydroxypropyl methyl cellulose and carboxymethyl cellulose, and starch derivatives, more particularly starch ethers and esters. Synthetic membrane materials are, for example, polymers such as polyacrylates, polyamides, polyvinyl alcohol or polyvinyl pyrrolidone. Examples of known microcapsules are the following commercial products (the membrane material is shown in brackets) Hallcrest Microcapsules (gelatin, gum arabic), Coletica Thalaspheres (maritime collagen), Lipotec Millicapseln (alginic acid, agar agar), Induchem Unispheres (lactose, microcrystalline cellulose, hydroxypropylmethyl cellulose), Unicetin C30 (lactose, microcrystalline cellulose, hydroxypropylmethyl cellulose), Kobo Glycospheres (modified starch, fatty acid esters, phospholipids), Softspheres (modified agar agar) and Kuhs Probiol Nanospheres (phospholipids).

Non-Pharmaceutical Applications

In addition, the invention is also directed to a number of non-pharmaceutical applications, in particular to the use of the extracts of *Nannochloropsis* for:

the treatment of human hair;
the treatment of human skin;
treatment of the human genitals;
modulating melanogenesis in human hair and/or human skin;
preventing and treating skin hyperpigmentation and spots;
modulating the growth and cycle of human hair and hair follicles;
modulating the fat metabolism in human hypodermis or subcutis;
improving and stimulating lipolysis;
modulating sebogenesis in human hair and/or human skin;
improving the hair appearance, in particular for treating greasy hair;
preventing and treating scalp disorders connected with excessive sebogenesesis, in particular for preventing and treating dandruff;
improving the skin appearance, in particular for treating oily skin;
modulating sebogenesis in the genital area and in particular in the human vulva.

Pharmaceutical Applications

An additional object of the present invention is related to extracts of *Nannochloropsis* sp. for use as a medicament in general and in particular use as a medicament for:
- treating or preventing disorders or dysfunctions connected to human skin melanogenesis;
- treating or preventing skin disorders or dysfunctions connected to excessive sebum production;
- treating or preventing hair loss by modulation of growth of human hair;
- treating or preventing hypodermal disorders by modulation of the adipocyte metabolism;
- treating or preventing dandruff;
- treating or preventing acne vulgaris;
- treating or preventing cellulite.

More particularly, the medicament relates to the treatment and/or prevention of dysfunctions of human hair and/or skin, such as:
- skin irritation;
- skin sensitization;
- scalp disorders connected with excessive sebogenesis;
- dandruff;
- hair loss;
- seborrhea;
- acne vulgaris;
- comedones;
- genital itching;
- skin disorders connected with skin pigmentation;
- melasma;
- disorders of the lipid metabolism in the human hypodermis;
- cellulite.

In the following, the invention is illustrated by—but not limited to—various working examples.

EXAMPLES

General Remarks

The extraction protocols were selected from many other technical solutions, and have to be considered as purely exemplificative. According to the present invention, freeze-dried biomasses were extracted with a liquid extractant selected from the group consisting of ethyl acetate, isopropanol, ethanol, methanol and water.

The extractant can also comprise a mixture of two or more of the above solvents. The extraction yields, expressed as percentage ratio between the dry extract and the dry weight of the microalgal material, are reported in Table 1. As the composition of the microalgae may change in relation to several environmental conditions, the extraction efficacy may also change, so the extract dry weights have to be considered as rough indications.

Finally, quantity and quality of compounds present in the extracts may vary with respect to both solvent properties and preparation protocol.

Activity of the Extracts on Hair Follicle Growth

Examples 1 to 8

Activity on the Growth of Hair Follicles of Ethyl Acetate (EtAc) Extract and Ethanol (EtOH) Extract Obtained from *Nannochloropsis* sp.

Hair follicles were taken from a single donor's scalp sample and transferred into sterile 24-well plates to be cultivated using a modified Williams' Medium E. Cultivation lasted for nine days, while the experimental treatment of the follicles started 24 hours from the beginning of the cultivation. Hair follicles were selected for the experiments after 18 h of cultivation. Only those follicles showing a good vital stage and a growth of not less than 0.2 mm were considered suitable to be maintained in culture. All experimental groups and the control were prepared comprising 12-18 follicles, plated in 24-well plates at a density of 3 hair follicles/well. The hair follicles showing evident signs of suffering during the culture for reasons not depending on the experimental treatment were excluded from the final analysis. The following experiment was conducted to demonstrate the activity on hair follicle growth of the ethyl acetate extract (EtAc) and ethanol extract (EtOH) obtained from *Nannochloropsis* sp. The extract was dried under vacuum and then dissolved in DMSO at a final concentration of 20,000 μg/ml. 0.5, 0.05, 0.005 or 0.0005 μl/ml of this stock solution was added to culture medium in order to obtain a final supplementation with extract at 10, 1, 0.1 and 0.01 μg/ml, respectively.

The growth performances observed in the treated hair follicles were compared to a control group cultured in the same culture medium without extract supplement. The activity of the treatment is demonstrated by the increase of growth of the hair follicles expressed as a variation of the average elongation of the experimental groups in comparison to the control group (Table 2). The experiment was terminated after 9 days of cultivation (8 of treatment). The growth of the hair follicles was studied by microphotography and subsequently determined by image analysis. All hair follicles were photographed at day 5 and day 9 of culture, respectively.

TABLE 2

Growth of hair follicles at day 9 of culture. Elongation expressed as % ratio of the control group performance.

| Example | Sample | Amount | Average | Std. error | Total no. of HFs |
|---|---|---|---|---|---|
| 0 | Control | 0 | 100.0 | 5.0 | 17 |
| 1 | EtAc | 0.01 μg/ml | 117.7 | 6.5 | 11 |
| 2 | EtAc | 0.1 μg/ml | 104.6 | 4.9 | 11 |
| 3 | EtAc | 1.0 μg/ml | 99.2 | 5.1 | 12 |
| 4 | EtAc | 10.0 μg/ml | 105.3 | 7.9 | 11 |
| 5 | EtOH | 0.01 μg/ml | 111.5 | 6.6 | 11 |
| 6 | EtOH | 0.1 μg/ml | 111.9 | 9.5 | 10 |
| 7 | EtOH | 1.0 μg/ml | 113.5 | 6.0 | 12 |
| 8 | EtOH | 10.0 μg/ml | 119.6 | 7.2 | 11 |

The treatment performed with 0.01 μg/ml of EtAc extract increased the follicle elongation by 18%, while all the EtOH extracts stimulated the hair growth by between 12% and 20% in comparison to the control group. These results show that the addition of these extracts leads to an increase in growth of the hair follicles.

The increase of hair growth, in culture conditions, can be achieved by improving the general health of the organ and/or by delaying the catagen, which physiologically occurs when the follicle is explanted from the scalp. Both these effects are strongly desirable and make the extracts very interesting for cosmetic applications, in particular as an ingredient for preparations aimed at combatting hair loss.

The experiment comparing different extracts attests that the actives can be extracted from the microalgae by using different solvents. However, it is also probable that the tested extracts differed from one another with regard to combination and composition in actives, therefore the responses detected, even if similar, might be produced by different compounds.

The detected stimulations have to be regarded as very intense, since the increase of hair growth usually recorded in response to treatments with positive controls (e.g. insulin and cyclosporine-a) can indicatively vary between 10% and 15%.

Activity on Melanogenesis

Melanocytes are the cell species responsible for melanogenesis both in skin and hair follicles. Melanin is the pigment accumulated in hair and skin and susceptible to be quantitatively modulated in response to sunlight exposure, aging processes and also pathological conditions.

The possibility of modulating melanogenesis is therefore a significant opportunity in cosmetics, for the relevance that body appearance has in social life, but also for the effective preservation of a healthy and young-looking condition of skin and hair.

The activity of the *Nannochloropsis* extracts on melanogenesis was studied by screening them on ex-vivo human skin cultures, that are sophisticated preclinical tests.

Assay Performed on Ex-Vivo Human Skin Culture

Organ cultures of ex-vivo human skin were performed starting from a skin sample, exciding cylindrical pieces of about 7 mm in diameter and culturing them up to day 6. The adopted culture medium was a modified William-E, and it was renewed at day three of the tissue culture. Samples of the extracts were air-dried and then dissolved in a quantity of DMSO suitable to obtain a final concentration of 1 and 10 µg/ml. On a daily basis, 4 µl of these extract preparations were applied topically to the cultured skin samples, while the control group received the same quantity of the pure DMSO. After six days of organ culture, histological sections were prepared from the skin samples, and quantitative changes of melanin content were investigated by adopting the Fontana-Masson staining technique. The variation in melanin content was estimated by image analysis of the microphotographs of histological sections of skin.

Examples 9 to 10

Activity on Melanogenesis of Ethanol Extract Obtained from *Nannochloropsis* sp.

Ethanol extract (EtOH) obtained from *Nannochloropsis* sp. was screened by treating human skin samples as described above. The results are shown in Table 3.

TABLE 3

Modulation of melanogenesis, evaluated in ex-vivo cultured human skin, following treatment with ethanol extract obtained from *Nannochloropsis* sp. Melanin content is expressed as % ratio of the control group performance.

| Example | Sample | Amount | Average | Std. error | No. of sections |
|---|---|---|---|---|---|
| 0 | Control | 0 | 100.0 | 6.3 | 12 |
| 9 | EtOH | 1.0 µg/ml | 83.3 | 5.2 | 12 |
| 10 | EtOH | 10 µg/ml | 94.6 | 6.8,0 | 12 |

The results attest that the treatment intensely inhibited melanogenesis. The decrease in melanin content varied from −5% to −17%.

Examples 11 to 12

Activity on Melanogenesis of Ethanol Extract Obtained from *Nannochloropsis* sp.

The previous experiment was replicated treating skin samples explanted from another donor. The results are summarized in Table 4.

TABLE 4

Modulation of melanogenesis, evaluated in ex-vivo cultured human skin, following treatment with ethanol extract obtained from *Nannochloropsis* sp. Melanin content is expressed as % ratio of the control group performance. The statistical significance was evaluated by means of One-way ANOVA with permutation test followed by pairwise post-hoc comparisons - Dunnett's permutation test

| Example | Sample | Amount | Average | Std. error | No. of sections | Statistics |
|---|---|---|---|---|---|---|
| 0 | Control | 0 | 100.0 | 5.6 | 12 | |
| 11 | EtOH | 1.0 µg/ml | 89.4 | 6.2 | 12 | n.s. |
| 12 | EtOH | 10 µg/ml | 72.2 | 8.2 | 12 | P < 0.01 |

The results confirm the skin lightening effect of the ethanol extract obtained from *Nannochloropsis*. The best response was detected following treatment with 10 µg/ml extract, which induced a 28% decrease in melanin content. This response is highly significant on a statistical basis.

Examples 13 to 14

Activity on Melanogenesis of Ethanol Extract Obtained from *Nannochloropsis* sp.

The previous experiment was replicated treating skin samples explanted from a third donor, including two treatments with retinoic acid as positive control. Retinoic acid is a well-known skin lightener. The results are summarized in Table 5.

TABLE 5

Modulation of melanogenesis, evaluated in ex-vivo cultured human skin, following treatment with ethanol extract obtained from *Nannochloropsis* sp. Melanin content is expressed as % ratio of the control group performance. The statistical significance was evaluated by means of One-way ANOVA with permutation test followed by pairwise post-hoc comparisons - Dunnett's permutation test

| Example | Sample | Amount | Average | Std. error | No. of sections | Statistics |
|---|---|---|---|---|---|---|
| 0 | Control | 0 | 100.0 | 4.3 | 10 | |
| 0 | Retinoic ac. | 10 µM | 82.4 | 6.5 | 10 | P < 0.05 |
| 0 | Retinoic ac. | 100 µM | 88.3 | 2.2 | 10 | n.s. |
| 13 | EtOH | 1.0 µg/ml | 81.1 | 3.9 | 10 | P < 0.05 |
| 14 | EtOH | 10 µg/ml | 81.2 | 4.1 | 10 | P < 0.05 |

The results confirmed the biological activity of the ethanol extract, which decreased the melanin content by 19% at both the tested concentrations. The biological activity of the experimental extract resulted as comparable or superior to that expressed by the positive control.

Examples 15 to 18

Activity on Melanogenesis of Ethanol Extract Obtained from *Nannochloropsis* sp.

The methods previously reported were adopted for testing the ethanol extract (EtOH) at concentrations comprised between 0.1 and 100 µg/ml, including a treatment with kojic acid (KA) as positive control. Kojic acid is a well-known skin lightener. The results are summarized in Table 6.

TABLE 6

Modulation of melanogenesis, evaluated in ex-vivo cultured human skin, following treatment with ethanol extract obtained from *Nannochloropsis* sp. Melanin content is expressed as % ratio of the control group performance. The statistical significance was evaluated by means of One-way ANOVA with permutation test followed by pairwise post-hoc comparisons - Dunnett's permutation test

| Example | Sample | Amount | Average | Std. error | No. of sections | Statistics |
|---|---|---|---|---|---|---|
| 0 | Control | 0 | 100.0 | 2.6 | 44 | |
| 0 | KA | 0.1% | 83.2 | 2.9 | 20 | P < 0.01 |
| 15 | EtOH | 0.1 µg/ml | 70.8 | 3.7 | 20 | P < 0.01 |
| 16 | EtOH | 1.0 µg/ml | 81.5 | 3.9 | 20 | P < 0.01 |
| 17 | EtOH | 10 µg/ml | 76.6 | 3.4 | 20 | P < 0.01 |
| 18 | EtOH | 100 µg/ml | 85.3 | 4.8 | 20 | P < 0.01 |

The results confirmed the biological activity of the ethanol extract, which reduced the skin melanin content at all the tested concentrations. The skin lightening was statistically very significant (P<0.01) on the basis of the adopted analysis. The activity of the extract resulted as comparable or more intense than the one expressed by the positive control.

Activity on Skin Inflammation Disclosed for the *Nannochloropsis* Extracts

Skin inflammation is a common problem that can occur in response to many causes. It can appear as occasional rashes accompanied by skin itching and redness, or chronic conditions such as dermatitis (eczema), rosacea, seborrheic dermatitis, and psoriasis.

The simple application of cosmetics is also sometimes sufficient to trigger an inflammatory reaction. This can occur because the preparation includes irritant compounds, and in this case the inflammatory reaction is quite fast, or as consequence of sensitizers, in which case the stimulus has to be repeated several times before the inflammatory reaction appears. In both cases, the inflammatory reaction requires the release of IL-1α by keratinocytes and so this cytokine is the ideal marker to adopt for screening compounds potentially having anti-inflammatory activity.

The following examples show that the extracts obtained from *Nannochloropsis* have a potent anti-inflammatory activity attested by the capacity to inhibit the IL-1α in skin samples treated with a typical irritant stimulus. This valuable effect, combined with the several beneficial activities already disclosed with regard to the hair follicle and skin, makes *Nannochloropsis* extracts ideal for cosmetic products as well as potential candidates for therapeutic applications.

Examples 19 to 20

Activity of Ethanol Extract Obtained from *Nannochloropsis* on Skin Inflammation (IL-1α Release) in Cultured Ex-Vivo Skin In order to study the biological activity of the ethanol extract (EtOH) from *Nannochloropsis* sp. on the inflammatory response of skin to irritation, the experimental protocol hereinafter summarized was adopted:
  i. ex-vivo skin samples (7 mm in diameter) were cultivated for 24 hours in 6-well plates (4 skin samples/well) with 2.5 ml/well of modified Williams E medium. The experimental design included the following experimental groups, each comprising 8 skin samples cultivated in 2 wells:
    1. control samples cultivated without receive any stimulus or treatment;
    2. samples stimulated with 2% SDS without subsequent lenitive treatment (negative control);
    3. samples stimulated with 2% SDS and then treated with dexamethasone at 10 µM (positive control).
    4. 2 groups of samples stimulated with 2% SDS and then treated with EtOH extract at 1 and 10 µg/ml respectively;
  ii. After 24 hours of culture the culture medium was renewed and the experimental groups 2 to 4 received the irritant stimulus (2% SDS) through topical application of 4 µl of preparation for each skin sample. After 3 hours the stimulus was removed by mean of cotton buds and 4 µl of lenitive treatment was then administered topically to groups 3 to 4. Stimulus treatments were applied in 50% DMSO, while the lenitive treatments were in pure DMSO.
  iii. After further 24 hours of cultivation, the culture media were collected separately from each group and the released IL-1α quantified via ELISA (BioLegend ELISAMAX cat. n. 434905).

Table 7 reports the average values of IL-1α obtained from the two medium samples (4 skin sample/well) collected for each experimental group.

TABLE 7

Activity of EtOH extracts obtained from *Nannochloropsis* on the IL-1α released by ex-vivo human skin samples stimulated with 2% SDS. In the last column the IL-1α release is expressed as percentage value assuming the concentration detected in the SDS group as reference (100%).

| Ex. | Sample | SDS Amount (stimulus) | Treatment Amount (lenitive) | IL-1α (pg/ml) | IL-1α release [%] |
|---|---|---|---|---|---|
| 0 | Control | 0 | 0 | 9.2 | 17.4 |
| 0 | SDS | 2% | 0 | 52.8 | 100.0 |
| 0 | Dexam. | 2% | 10 µM | 48.6 | 92.2 |
| 19 | EtOH | 2% | 1.0 µg/ml | 46.6 | 88.3 |
| 20 | EtOH | 2% | 10 µg/ml | 42.1 | 79.8 |

The results attest that the irritant stimulus produced the expected effect, since the IL-1α released in the medium increased from 9.2 pg/ml to 52.8 pg/ml. Surprisingly, the treatments with *Nannochoropsis* extract extenuated the inflammatory response, decreasing the IL-1α release from 11.7% to 20.2% in comparison with the SDS group. Interestingly, the extract effect was superior to the treatment adopted as positive control, obtained by administering dexamethasone, a potent steroid glucocorticoid.

Examples 21 to 24

Activity of Ethyl Acetate (EtAc) and Aqueous (Water) Extracts Obtained from *Nannochloropsis* Sp. on Skin Inflammation (IL-1α Release) in Cultured Ex-Vivo Skin A second experiment was performed on ex-vivo skin culture in order to study the biological activity of the ethyl acetate (EtAc) extract and aqueous (water) extract obtained from *Nannochloropsis* sp. on the inflammatory response of skin to irritation. The experiment was conducted following the protocol adopted for the previous experiment. Table 8 reports the average values of IL-1α obtained from the two medium samples (4 skin sample/well) collected for each experimental group.

TABLE 8

Activity of EtAc and water extracts obtained from *Nannochloropsis* on the IL-1α released by ex-vivo human skin samples stimulated with 2% SDS. In the last column the IL-1α release is expressed as percentage value assuming the concentration detected in the SDS group as reference (100%).

| Ex. | Sample | SDS Amount (stimulus) | Treatment Amount (lenitive) | IL-1α (pg/ml) | IL-1α release [%] |
|---|---|---|---|---|---|
| 0 | Control | 0 | 0 | 8.4 | 32.0 |
| 0 | SDS | 2% | 0 | 26.2 | 100.0 |
| 21 | EtAc | 2% | 1.0 µg/ml | 14.9 | 56.8 |
| 22 | EtAc | 2% | 10 µg/ml | 16.8 | 64.0 |
| 23 | Water | 2% | 1.0 µg/ml | 22.9 | 87.5 |
| 24 | Water | 2% | 10 µg/ml | 20.5 | 78.3 |

The results attest that the two experimental extracts produced an anti-inflammatory effect, since the lenitive treatments reduced the IL-1α release from 12.5% to 43.2% in comparison with the group treated with SDS only. However, the more intense lenitive response was detected following the treatment with EtAc extract, which reduced the release of IL-1α by 36.0-43.2% in comparison with the SDS group.

Activity on Human Adipocyte Metabolism Disclosed for Extracts Obtained from *Nannochloropsis*

In order to evaluate the presence in *Nannochloropsis* of natural compounds active on the lipid metabolism, full-thickness human skin samples with subcutis were cultured ex-vivo and treated systematically with different extracts obtained from the microalgae.

The responses of the treated tissues, in comparison to the untreated group, were evaluated after 6 days of culture, by isolating the subcutis of each skin sample and then estimating its normalized content in total lipids.

Examples 25 to 30

Activity of Ethyl Acetate (EtAc), Ethanol (EtOH) and Aqueous (Water) Extracts Obtained from *Nannochloropsis* sp. on the Lipid Metabolism of the Skin Subcutis The following experiment was conducted to demonstrate the activity on adipocyte metabolism of the ethyl acetate extract (EtAc), ethanol extract (EtOH) and aqueous extract obtained from *Nannochloropsis* sp. All the extracts were prepared as stock solutions at 5,000 µg/ml. The solvent of the EtAc extract was evaporated under vacuum and then the dry extract was dissolved in EtOH at the final concentration of 5,000 µg/ml.

The experimental culture media were prepared adding 2.0 µl/ml or 0.2 µl/ml of each stock solution, in order to obtain final extract concentrations of 10 and 1.0 µg/ml, respectively. Since the medium supplemented with EtAc and EtOH extracts at 10 µg/ml contained 0.2% ethanol, the same amount of ethanol was added to the other culture media in the experiment, including the control.

Organ cultures of full thickness human skin with subcutis were performed starting from a skin sample, exciding cylindrical pieces of 7 mm in diameter and culturing them up to day 6. The excised samples were prepared paying attention to preserve the subcutis and their cultivation was done in 24-well plates, seeding a sample/well with 500 µl of culture medium. The control received modified William E medium, while the samples submitted to experimental treatment received the same medium supplemented with the extracts. The culture medium was renewed every other day. Each group of the experimental design was composed of four skin samples. After six days of organ culture, the subcutis of each skin sample was excised from the dermis and its content in total lipids was quantified. In order to make the values of total lipids detected in different samples comparable, it was necessary to normalize them for the total proteins. In fact, the stimulation of lipogenesis in the subcutis promotes synthesis and storage of lipids, while it does not substantially affect the metabolism of the structural proteins. As a result, when lipogenesis is stimulated, an increase in the "total lipids/total proteins ratio", hereinafter defined "normalized total lipids", is expected, while the contrary occurs in the case of increased lipolysis. The analytical protocol adopted to detect values of "normalized total lipids" is as follows:

1. each subcutis sample was homogenized in 1 ml of isopropyl alcohol;
2. the sample was centrifuged at 14,000 G for 5 minutes and then the supernatant (containing the extracted lipids) was collected;
3. the supernatant was diluted 10 fold with isopropyl alcohol;
4. the diluted lipid extract was analyzed using a Direct Detect IR Spectrometer (Millipore), which provides the total lipid concentration expressed in mg/ml;
5. the total lipids of the subcutis sample were quantified multiplying the supernatant lipid concentration (indention 4) by the preliminary dilution factor (indention 3) and then by the volume of isopropyl alcohol adopted for the lipid extraction (indention 1);
6. the residual pellet obtained from indention 2 was washed with 1 ml of isopropyl alcohol and, after a further centrifugation, this solvent was withdrawn;
7. the pellet was dried in a vacuum dry evaporator and then again homogenized in 0.1 ml of proteolytic buffer (20 mM Tris HCl pH 7.5, 150 mM NaCl, 2 mM EDTA, 0.5% Triton X-100, 2 mM DTT, 1% protease inhibitor cocktail);
8. the extractive mixture was incubated for a suitable time and then centrifuged at 14,000 G for 10 minutes and the supernatant was collected and analyzed using a Direct Detect IR Spectrometer (Millipore), which provides the total protein concentration expressed in mg/ml;
9. the obtained total protein concentration was multiplied by the extractive volume (indention 7) in order to quantify the total proteins of the subcutis sample;
10. the total lipids (indention 5) were divided by the total proteins (indention 9) in order to obtain the amount of lipids per mg of proteins relative to the processed subcutis sample.

Table 9 shows the normalized total lipids of the experimental groups, expressed as percentage value assuming the normalized total lipids detected in the control group as reference (100%).

TABLE 9

Variation of total lipids in human skin samples treated with ethyl acetate extract (EtAc), ethanol extract (EtOH) and aqueous extract (water) obtained from *Nannochloropsis*. The data are expressed as % ratio of the control group value (100%). The statistical significance was evaluated by means of One-way ANOVA with permutation test followed by pairwise post-hoc comparisons - Dunnett's permutation test

| Example | Sample | Amount | Average | Std. error | No. skin samples | Statistics |
|---|---|---|---|---|---|---|
| 0 | Control | 0 | 100.0 | 6.4 | 4 | |
| 25 | EtAc | 1.0 µg/ml | 77.2 | 5.9 | 4 | n.s. |
| 26 | EtAc | 10 µg/ml | 60.0 | 5.4 | 4 | P < 0.01 |

TABLE 9-continued

Variation of total lipids in human skin samples treated with ethyl acetate extract (EtAc), ethanol extract (EtOH) and aqueous extract (water) obtained from *Nannochloropsis*. The data are expressed as % ratio of the control group value (100%). The statistical significance was evaluated by means of One-way ANOVA with permutation test followed by pairwise post-hoc comparisons - Dunnett's permutation test

| Example | Sample | Amount | Average | Std. error | No. skin samples | Statistics |
|---|---|---|---|---|---|---|
| 27 | EtOH | 1.0 µg/ml | 59.7 | 6.2 | 4 | P < 0.01 |
| 28 | EtOH | 10 µg/ml | 54.8 | 6.2 | 4 | P < 0.01 |
| 29 | Water | 1.0 µg/ml | 75.7 | 2.0 | 4 | P < 0.05 |
| 30 | Water | 10 µg/ml | 97.9 | 5.6 | 4 | n.s. |

The experimental results attest that all the extracts decreased the amount of lipids in the skin subcutis. The more intense responses were detected following the treatments with 1.0-10 µg/ml EtOH extract and 10 µg/ml EtAc extract, which induced a highly significant decrease of lipids on a statistical basis (p<0.01). However, the 1.0 µg/ml water extract also produced a significant decrease (p<0.05) of lipids according to the statistical analysis used.

These data show that the extracts obtained from *Nannochloropsis* can significantly affect the metabolism of lipids and can be adopted for combatting undesired accumulation of hypodermal fat, as in the case of cellulite.

Activity of *Nannochloropsis* Extracts on Human Sebaceous Glands

In order to evaluate the presence in *Nannochloropsis* sp. of natural compounds active on sebogenesis, ex-vivo cultures of human sebaceous glands (hSGs) were set up and treated with different extracts obtained from this microalga.

The responses of the treated hSGs, in comparison to the untreated group, were evaluated after 6 days of culture by analyzing their total lipid content and normalizing this value to the protein amount present in their composition, as already explained discussing the lipid quantification of the skin subcutis.

Examples 31 to 36

Activity of Ethyl Acetate (EtAc), Ethanol (EtOH) and Aqueous (Water) Extracts Obtained from *Nannochloropsis* on the Lipid Metabolism of Human Sebaceous Glands (hSGs)

The extracts adopted in the previous experiment were also screened to evaluate their activity on sebogenesis. The experimental culture media extracts were prepared following the procedure described for the previous experiment.

Using micro-scissors and tweezers, hSGs were isolated from the pilosebaceous units of a scalp skin sample. They were seeded in 24-well plates at a density of 8 hSGs/well and then cultivated in 500 µl of modified William E medium. After 24 hours of culture, the viability of the hSGs was assessed by means of resazurine assay. Following the confirmation of the good viability of the cultured organs, the experimental treatments were started and continued up to day 6. The control received modified William E medium, while the samples submitted to experimental treatments received the same medium supplemented with the extracts. The culture medium was renewed every other day. After six days of organ culture, the viability of the hGSs was again assessed via resazurine assay and then, having attested their good condition, each group of hGSs was collected and analyzed according the following protocol:

1. each hSG group was homogenized in 0.1 ml of isopropyl alcohol;
2. the sample was centrifuged at 14,000 G for 5 minutes and then the supernatant (containing the extracted sebum) was collected;
3. the sebum extract was analysed in triplicate using a Direct Detect IR Spectrometer (Millipore), which provided the total lipid concentration of the supernatant (mg/ml);
4. the total lipids of the hSGs were quantified multiplying the supernatant lipid concentration (indention 3) by the volume of isopropyl alcohol adopted for the lipid extraction (indention 1);
5. the pellet remaining from indention 2 was dried in a vacuum dry evaporator and then again homogenized in 0.05 ml of proteolytic buffer (20 mM Tris/HCl pH 7.5, 150 mM NaCl, 2 mM EDTA, 0.5% Triton X-100, 2 mM DTT, 1% protease inhibitor cocktail);
6. this extractive mixture was centrifuged at 14,000 G for 10 minutes and the supernatant was collected and analyzed in triplicate using a Direct Detect IR Spectrometer (Millipore);
7. the obtained total protein concentration was multiplied by the extractive volume (indention 5) in order to quantify the total proteins of the hSGs;
8. the total lipid amount (indention 4), i.e. the amount of sebum, was divided by the total proteins (indention 7) in order to obtain the normalized amount of lipids per mg of proteins (mg of lipids/mg of proteins).

This experimental design included two different positive controls selected from commercial compounds active on sebogenesis: 5α-Avocuta (Butyl-Avocadate), which is an active ingredient derived from avocado pears, and Asebiol™, a commercial active product formulated combining aminoacids, sulphated peptides, vitamin B complex and allantoin.

The amounts of normalized total lipids obtained from the treated groups, i.e. the sebum produced by each group of hSGs, were expressed in percentage values with respect to the value obtained in the control group and the results are shown in Table 10.

TABLE 10

Variation of sebum in hSGs treated with ethyl acetate extract (EtAc), ethanol extract (EtOH) and aqueous extract (water) obtained from *Nannochloropsis*. The data are expressed as % ratio of the control group value. The statistical significance was evaluated by means of One-way ANOVA with permutation test followed by pairwise post-hoc comparisons - Dunnett's permutation test

| Example | Sample | Amount | Average | Std. error | Statistics |
|---|---|---|---|---|---|
| 0 | Control | 0 | 100.0 | 1.0 | |
| 0 | 5α-Avocuta | 0.1% | 82.4 | 1.6 | P < 0.01 |
| 0 | Asebiol ™ | 0.1% | 82.4 | 2.7 | P < 0.01 |
| 31 | EtAc | 0.1 µg/ml | 83.6 | 2.3 | P < 0.01 |
| 32 | EtAc | 1.0 µg/ml | 66.9 | 1.5 | P < 0.01 |
| 33 | EtOH | 0.1 µg/ml | 69.0 | 1.1 | P < 0.01 |
| 34 | EtOH | 1.0 µg/ml | 80.2 | 1.9 | P < 0.01 |
| 35 | Water | 0.1 µg/ml | 61.1 | 1.1 | P < 0.01 |
| 36 | Water | 1.0 µg/ml | 77.3 | 1.2 | P < 0.01 |

The results attest that all the extracts inhibited sebum production, inducing a decrease that ranged between 16.4% and 38.9%. The activity of the extracts was comparable or superior to those expressed by the positive controls. These data show that *Nannochloropsis* synthesizes some compounds suitable to be exploited as seboregulators. These compounds have different lipophilic affinity and can be separately extracted with lipophilic solvents as well as with hydrophilic solvents.

Examples 37 to 38

Activity of Ethyl Acetate (EtAc) Extract Obtained from *Nannochloropsis* sp. on the Lipid Metabolism of Human Sebaceous Glands (hSGs)

The ethyl acetate extract was newly tested on hSGs taken from another donor, adopting the same methods described for the previous examples. As positive control, a 5 µM Capsaicin treatment was included in the experiment. The amounts of normalized total lipids obtained from the treated groups, expressed in percentage values with respect to the value obtained in the control group, are shown in Table 11.

TABLE 11

Variation of sebum in hSGs treated with ethyl acetate extract (EtAc) extract obtained from *Nannochloropsis*. The data are expressed as % ratio of the control group value. The statistical significance was evaluated by means of One-way ANOVA with permutation test followed by pairwise post-hoc comparisons - Dunnett's permutation test

| Example | Sample | Amount | Average | Std. error | Statistics |
|---------|--------|--------|---------|------------|------------|
| 0 | Control | 0 | 100.0 | 1.4 | |
| 0 | Capsaicin | 5 µM | 66.5 | 1.3 | $P < 0.01$ |
| 37 | EtAc | 0.1 µg/ml | 71.4 | 0.5 | $P < 0.01$ |
| 38 | EtAc | 1 µg/ml | 51.4 | 0.9 | $P < 0.01$ |

The results attest that the EtAc extract inhibited sebum production in a measure comparable with the positive control. The produced inhibition is very significant on the basis of the statistical analysis adopted.

Examples 39 to 40

Activity of Ethanol (EtOH) Extract Obtained from *Nannochloropsis* sp. on the Lipid Metabolism of Human Sebaceous Glands (hSGs)

The ethanol extract was newly tested on hSGs taken from another donor, adopting the same methods described for the previous examples. As positive control, a 5 µM Capsaicin treatment was included in the experiment. The amounts of normalized total lipids obtained from the treated groups, expressed in percentage values with respect to the value obtained in the control group, are shown in Table 12.

TABLE 12

Variation of sebum in hSGs treated with ethanol (EtOH) extract obtained from *Nannochloropsis*. The data are expressed as % ratio of the control group value. The statistical significance was evaluated by means of One-way ANOVA with permutation test followed by pairwise post-hoc comparisons - Dunnett's permutation test

| Example | Sample | Amount | Average | Std. error | Statistics |
|---------|--------|--------|---------|------------|------------|
| 0 | Control | 0 | 100.0 | 2.5 | |
| 0 | Capsaicin | 5 µM | 91.9 | 1.3 | $P < 0.01$ |
| 39 | EtOH | 0.1 µg/ml | 93.7 | 1.1 | $P < 0.05$ |
| 40 | EtOH | 1 µg/ml | 79.4 | 1.1 | $P < 0.01$ |

The results attest that the ethanol extract inhibited the sebum production in a measure comparable or higher than the positive control. The produced inhibition is significant ($P<0.05$) or very significant ($P<0.01$) on the basis of the statistical analysis adopted.

Examples 41 to 43

Activity of Aqueous (Water) Extract Obtained from *Nannochloropsis* sp. on the Lipid Metabolism of Human Sebaceous Glands (hSGs)

The aqueous extract was tested on hSGs taken from another donor, adopting the same methods described for the previous examples. As positive control, a 5 µM Capsaicin treatment was included in the experimental design. The amounts of normalized total lipids obtained from the treated groups, expressed in percentage values with respect to the value obtained in the control group, are shown in Table 13.

TABLE 13

Variation of sebum in hSGs treated with aqueous extract (water) obtained from *Nannochloropsis*. The data are expressed as % ratio of the control group value. The statistical significance was evaluated by means of One-way ANOVA with permutation test followed by pairwise post-hoc comparisons - Dunnett's permutation test

| Example | Sample | Amount | Average | Std. error | Statistics |
|---------|--------|--------|---------|------------|------------|
| 0 | Control | 0 | 100.00 | 1.8 | |
| 0 | Capsaicin | 5 µM | 45.6 | 0.4 | $P < 0.01$ |
| 41 | Water | 0.1 µg/ml | 90.7 | 0.9 | $P < 0.01$ |
| 42 | Water | 1 µg/ml | 74.3 | 1.0 | $P < 0.01$ |
| 43 | Water | 10 µg/ml | 66.4 | 1.1 | $P < 0.01$ |

The results attest that the aqueous extract inhibited sebum production in a very significant ($P<0.01$) measure on the basis of the statistical analysis adopted.

What claimed is:

1. A method for the treatment of a human hair or skin condition selected from the group consisting of human skin melanogenesis, skin hyperpigmentation, skin spots, hair loss, hypodermal disorders, cellulite, reducing growth of human hair, and adipocyte metabolism comprising topically administering on the skin or scalp of a subject in need thereof, an extract of *Nannochloropsis* sp. obtained by the steps of:
   (a) bringing microalgae in contact with a solvent selected from the group consisting of C1-C4 aliphatic alcohols, ethyl acetate, and mixtures thereof, and mixtures of C1-C4 aliphatic alcohols with water, in an amount suitable to make active move into the solvent phase,
   (b) removing the dissolved extract from the residue, and
   (c) recovering the pure extract from the solvent,
   in an amount effective for fighting or preventing disorder or dysfunction connected to human skin melanogenesis, or skin hyperpigmentation and spots, or
   hypodermal disorders by modulation of adipocyte metabolism, or
   cellulite,
   in an amount effective for modulating
   growth of human hair, or
   the adipocyte metabolism, or
   the skin melanogenesis.

2. The method according to claim 1, comprising (a) extracting with a mixture of two or more of said solvents.

3. The method according to claim 1, wherein (a) the solvent is ethyl acetate.

4. The method according to claim 1, wherein (a) the solvent is ethanol.

5. The method according to claim 1, wherein the extract of *Nannochloropsis* sp.is combined with a cosmetically acceptable carrier selected from the group consisting of C1-C4 aliphatic alcohols, polyols having 3 to 12 carbon atoms, oil components, water, and mixtures thereof.

6. The method according to claim 1, wherein *Nannochloropsis* sp. are *N. granulate, N. limnetica, N. oceanica* or *N. oculata*.

7. A method for the treatment of a human hair or skin condition selected from the group consisting of human skin melanogenesis, skin hyperpigmentation, skin spots, hair loss, hypodermal disorders, cellulite, reducing growth of human hair, and adipocyte metabolism consisting of topically administering on the skin or scalp of a subject in need thereof, an extract of *Nannochloropsis* sp. obtained by the steps consisting of:
 (a) bringing microalgae in contact with a solvent selected from the group consisting of C1-C4 aliphatic alcohols, ethyl acetate, and mixtures thereof, and mixtures of C1-C4 aliphatic alcohols with water, in an amount suitable to make active move into the solvent phase,
 (b) removing the dissolved extract from the residue, and
 (c) recovering the pure extract from the solvent,
 in an amount effective for fighting or preventing
  disorder or dysfunction connected to human skin melanogenesis, or
  skin hyperpigmentation and spots, or
  hypodermal disorders by modulation of adipocyte metabolism, or
  cellulite,
 in an amount effective for modulating
  growth of human hair, or
  the adipocyte metabolism, or
  the skin melanogenesis.

\* \* \* \* \*